(12) United States Patent
Jordan et al.

(10) Patent No.: US 7,846,919 B2
(45) Date of Patent: *Dec. 7, 2010

(54) CHELATED 8-HYDROXYQUINOLINE AND USE THEREOF IN A METHOD OF TREATING EPITHELIAL LESIONS

(75) Inventors: Russel T. Jordan, Fort Collins, CO (US); Carl C. Hanson, Parker, CO (US); Frank S. Potestio, Parker, CO (US)

(73) Assignee: Dermex Pharmaceuticals, LLC, Parker, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/021,421

(22) Filed: Feb. 10, 1998

(65) Prior Publication Data

US 2004/0092496 A1 May 13, 2004

(51) Int. Cl.
*A61K 31/555* (2006.01)
*A61K 31/47* (2006.01)
*A61K 31/32* (2006.01)

(52) U.S. Cl. .................. 514/187; 514/312; 424/641
(58) Field of Classification Search .............. 514/187, 514/312; 424/49, 641
See application file for complete search history.

(56) References Cited

U.S. PATENT DOCUMENTS

| | | | |
|---|---|---|---|
| 3,637,772 A * | 1/1972 | Klaui et al. ............... | 554/3 |
| 4,469,702 A | 9/1984 | Schulte | |
| 4,766,113 A * | 8/1988 | West et al. ............... | 514/187 |
| 4,780,320 A * | 10/1988 | Baker ..................... | 424/493 |
| 4,868,172 A | 9/1989 | Sebestyen et al. | |
| 5,536,502 A | 7/1996 | Mulder | |
| 5,605,700 A | 2/1997 | DeGregorio et al. | |
| 5,684,169 A | 11/1997 | Hamada et al. | |
| 5,817,675 A | 10/1998 | Whitefield | |
| 6,124,374 A * | 9/2000 | Kolias et al. ............. | 523/120 |
| 6,476,014 B1 | 11/2002 | Jordan et al. | |
| 6,774,124 B2 | 8/2004 | Jordan et al. | |

FOREIGN PATENT DOCUMENTS

| | | | |
|---|---|---|---|
| AU | 199925956 | 4/2003 | |
| EP | 0506207 A2 * | 3/1985 | .......... 514/187 |
| EP | 0 506 207 A2 | 9/1992 | |
| EP | 0506207 A2 | 9/1992 | |
| EP | 0634170 | 6/2004 | |
| GB | 1215676 * | 12/1970 | .......... 514/187 |
| GB | 2 189 144 A | 10/1987 | |
| WO | WO 88/03805 * | 6/1988 | |
| WO | 95/03032 * | 2/1995 | |
| WO | WO99/39721 | 8/1999 | |

OTHER PUBLICATIONS

Kazimierczak, W. and Maslinski, C. Histamine Release from Mast Cells by Compound 48/80. The Membrane Action of Zinc. Agents and Actions, vol. 4/5 (1974), p. 320-323.*
The Merck Index 12th Edition, 1996, Merck & Co., publ., p. 832 (Entry 4890).*
Cosmetic Ingredient Review; Ingredient Publication Status, Jun. 24, 1994; 24 pages.
Selective Toxicity by Adrien Albert; 1965; pp. 334-391.
Specifications 6092H; 8-Hydroxyquinoline; 8-Quinolinol; Oxine by Karl Fischer (1 page).
Nordenberg et al., "Anti-proliferative Effects and Phenotypic Alterations Induced by 8-hydroxyquinoline in Melanoma Cell Lines," Eur J. Cancer (Great Brintain), vol. 26 (No. 8), p. 905-907.
Kazimierczak, W. & Maslinski, C. Histamine Release From Mast Cells by Compound 48/80. The Membrane Action of Zinc. Agents and Actions, vol. 4/5 (1974), p. 320-323.
Cosmetic Ingredient Review; Ingredient Publication Status, Jun. 24, 1994; 24 pages.
Albert, A.; Selective Toxicity; 1965; pp. 334-391.
Specifications 6092H; 8-Hydroxyquinoline; Oxine by Karl Fischer (1 page); undated.
Related U.S. Appl. No. 10/247,526; Notice of Allowability; Dec. 2, 2003.
Related U.S. Appl. No. 10/247,526; Preliminary Amendment; Dec. 19, 2002.
Related U.S. Appl. No. 11/434,613; Office Action Mailed Aug. 30, 2007.
Related U.S. Appl. No. 10/247,161; Preliminary Amendment filed Dec. 9, 2002.
Related U.S. Appl. No. 10/247,161; Notice of Allowability; Dec. 27, 2005.

(Continued)

*Primary Examiner*—James D Anderson
(74) *Attorney, Agent, or Firm*—Lathrop & Gage LLP

(57) ABSTRACT

Oxinates including 8-hydroxyquinoline and a heavy metal are topically applied to epidermal lesions for therapeutic effect. The zinc oxinate compositions are shown to be therapeutically effective against The therapeutic composition demonstrates selective toxicity with a therapeutic index of one-hundred percent on human lung cancer, breast cancer, melanoma, venereal warts, male veruoca warts, lesions produced by human papilloma virus, basal cell carcinoma, solar keratosis, and Kaposi's sarcoma. In veterinary applications where dogs, cats, and horses are the patients, the composition shows a one-hundred percent therapeutic index with selective toxicity against eye cancer, sarcoids, sarcoma, malignant melanoma, rectal adenoma, histiocytoma, and sebaceous adenoma.

16 Claims, 1 Drawing Sheet

OTHER PUBLICATIONS

NZ506367 Dermex Pharmaceticals; Abstract only; Mar. 28, 2003.
DE69935037D Dermex Pharmaceuticals; Abstract only; Mar. 22, 2007.
Related U.S. Appl. No. 10/247,161; Office Action mailed Dec. 19, 2003.
Related U.S. Appl. No. 10/247,161; Response to Office Action mailed Dec. 19, 2003.
Related U.S. Appl. No. 10/247,161; Office Action mailed Sep. 23, 2004.
Related U.S. Appl. No. 10/247,161; Response to Office Action mailed Sep. 23, 2004.
Related U.S. Appl. No. 10/247,161; Office Action mailed Apr. 21, 2005.
Related U.S. Appl. No. 10/247,161; Response to Office Action mailed Apr. 21, 2005.
Related U.S. Appl. No. 09/601,304; Office Action mailed Oct. 24, 2001.
Related U.S. Appl. No. 09/601,304; Response to Office Action mailed Apr. 24, 2002.
Related U.S. Appl. No. 09/601,304; Notice of Allowance mailed Jun. 18, 2002.
Related U.S. Appl. No. 09/601,304; Response to Notice of Allowance mailed Sep. 18, 2002.
Related U.S. Appl. No. 09/601,304; Response to the Amendment of Notice of Allowance mailed Oct. 3, 2002.
Office Action dated Jun. 23, 2010 issued in related U.S. Appl. No. 11/434,613, 10 pages.

* cited by examiner

CHELATED 8-HYDROXYQUINOLINE AND USE THEREOF IN A METHOD OF TREATING EPITHELIAL LESIONS

BACKGROUND OF THE INVENTION

1. Field of the Invention

The present invention pertains to the field of oxinates and, particularly, to the therapeutic use of chelated metal 8-hydroxyquinolinates in the treatment of cancers, precancerous lesions, and other abnormal tissues.

2. Statement of the Problem

A preferred treatment modality for many cancers is surgical excision of the cancerous lesion. Surgical excision is not always desirable when surgery could sever nerves or produce scars that interfere with normal movements in tissues proximate the site of surgery.

Chemicals have been developed to treat cancers. Rate-sensitive cytotoxic drugs have cytotoxic effects on all tissue types, but are particularly effective against certain cancers that function at a metabolic rate greater than the metabolic rate of normal cells. The increased metabolic rate of these cancers makes them more susceptible to the cytotoxicity of the drugs. In this manner it is possible to provide a dosage that is fatal to cancer cells, while that same dosage is not fatal to normal cells. By way of example, U.S. Pat. No. 5,684,169 teaches the formation of cyclodextrin complexes of taxol to improve the solubility of taxol in water. Taxol is a cytotoxic drug that is believed to attack and kill cancer cells with a rate-sensitive effect.

Other chemicals are specifically designed for the treatment of skin cancers and cancers that reside close to the skin. U.S. Pat. No. 5,605,700 describes a transdermal preparation containing toremifene for use in treating cancers of the skin or cancers that reside a short distance from the skin, such as metastic lesions of breast cancer. The transdermal preparations are said to be of particular interest in the treatment of melanoma, lymphoma, Kaposi's sarcoma, and fungoides mycosis. Escharotics or caustic chemicals, such as Podophylin or tricholoroacetic acid which are used in the treatment of skin cancer, venereal warts and human papilloma virus, are designed to produce a chemical burn that destroys substantially all of the tissues in contact with the chemical. None of these chemicals is selective in destroying only the lesion while leaving behind healthy tissues that exist close to the site of the lesion, i.e., the chemicals lack selectivity and specificity.

The chemical 8-hydroxyquinoline is not used for the treatment of epithelial lesions, such as epitheliomas and venereal warts. 8-hydroxyquinoline is known by various other names including oxine, 8-hydroxy-chinolin, hydroxybenzopyridine, and 8-oxyquiniline. The federal government has approved 8-hydroxyquinoline for cosmetic use in low concentrations of less than five percent. At these concentrations, 8-hydroxyquinoline functions as a cosmetic biocide, as reported in JACT 11(4), 1992. U.S. Pat. No. 4,302,467 reports the use of 8-hydroxyquinoline or its chelates in combination with dehydroacetic acid or sorbic acid. The combination is reported to work synergistically against bacteria and fungus. According to the Merck Index 11th Edition, Merck & Co. publ., p. 4779. (1989), 8-hydroxyquinoline is used as a fungistat, a chelating agent in the determination of trace metals, and a disinfectant.

Chapter ten of the book Albert, Selective Toxicity 3rd Ed., New York, John Wiley & Sons, Inc. (1965) states on page 370-378 that the antibacterial action of oxine is due to chelation. Iron-chelated forms of oxine are toxic to gram-positive bacteria when mixed with $Fe^{3+}$ at a 1:1 molar ratio and a 1:2 molar ratio of oxine to iron, but toxicity diminishes at a 1:3 ratio. Despite its strong antibacteriological effects, oxine and its derivatives are not normally injected into the bloodstream because they are inactivated by red blood cells, which secrete a substance that binds oxine.

There remains a need for a topically applied therapeutic composition with selective toxicity in the treatment of epithelial lesions.

Solution

The present invention overcomes the problems that are outlined above by providing a topically applied therapeutic composition having selective toxicity in the treatment of epithelial lesions. The therapeutic composition demonstrates selective toxicity on human lung cancer, breast cancer, and melanoma. Furthermore, the composition has been used to treat human patients where it demonstrates a one-hundred percent therapeutic index with selective toxicity against venereal warts, male veruoca warts, lesions produced by human papilloma virus, basal cell carcinoma, solar keratosis, and Kaposi's sarcoma. In veterinary applications where dogs, cats, and horses are the patients, the composition shows a one-hundred percent therapeutic index with selective toxicity against eye cancer, sarcoids, sarcoma, malignant melanoma, rectal adenoma, histiocytoma, and sebaceous adenoma. In this context, the therapeutic index is defined as the number of patients cured divided by the number of patients treated.

A therapeutic composition according to the present invention contains 8-hydroxyquinoline or a functional homologue thereof, a chelatable metal agent, and a carrier. The 8-hydroxyquinoline and the chelatable metal agent are present in effective amounts for treating mammalian epithelial lesions selected from the group consisting of cancerous lesions, precancerous lesions, and warts. These mammalian epithelial lesions specifically include venereal warts, male veruoca warts, lesions produced by human papilloma virus, basal cell carcinoma, solar keratosis, Kaposi's sarcoma, eye cancer, sarcoids, sarcoma, malignant melanoma, rectal adenoma, histiocytoma, and sebaceous adenoma.

Therapeutically effective amounts include therapeutically effective concentrations, as well as therapeutically effective ratios of the 8-hydroxyquinoline and the chelatable metal agent. The preferred range for therapeutically effective ratio is one wherein the molar ratio of 8-hydroxyquinoline to the chelatable metal agent ranges from 1:1 up to 1:N, where N is the oxidation state of the chelatable metal. At the ratio of 1:N, the chelated oxine is easily transported across the cell membrane because it has a neutral charge. Charged species are also observed to be threrapeutically effective. Where the metal has a valence of +2, therapeutically effective ratios range from 1:1 to 1:3, and the most preferred ratio is about 1:2. The 8-hydroxyquinoline is preferably present in an amount ranging from five percent to twenty percent of the composition by weight, and the most preferred amount of 8-hydroxyquinoline is about ten percent by weight.

As stated above, the therapeutic compositions include a chelatable metal agent. This agent is preferably a chelatable metal bonded to a halogen, which yields an ionic species of the metal in solution. This reaction is free for covalent and coordinate bonding with oxine in solution. The metal is preferably a heavy metal or a transition metal. Heavy metals are more preferred, and the preferred heavy metals are copper, iron, manganese, molybdenum, and cobalt. Zinc is the most preferred heavy metal. The metal is preferably provided as a salt including a metal and a halogen. Chlorine is the most preferred halogen. Thus, the most preferred chelatable metal is provided as zinc chloride.

The carrier is preferably formed of a gel base to enhance the time during which the composition is retained on the epithelial lesion where it is applied. Lecithin is preferably added as a penetrating agent, and the penetrating effect of lecithin may be enhanced by the use of dimethyl sulfoxide (DMSO). The carrier also contains an emollient, such as isopropyl palmitate or isopropyl myristate. The gel base is made of a hydrophilic polymer, such as polyacrylamide or polyoxyalkylene derivatives of propylene glycol. A topical steroid, such as 1-2% hydrocortizone may be added to decrease the incidence or severity of contact dermatitis proximate the site of topical application.

A further preferred aspect of the invention is the use of antioxidants to stabilize chelated 8-hydroxyquinoline in vivo. Noridydroguiaretic acid, derivatives of noridydroguiaretic acid, and functional homologues of noridydroguiaretic acid stabilize zinc-chelated 8-hydroxyquinoline against inactivation by thermolabile substances in the blood for solutions that are injected into the body. Similarly, 8-hydroxyquinoline and zinc chloride coprecipitated with sodium ascorbate forms a stable orally administrable product having therapeutic efficacy.

The composition is administered to the epithelial lesion by topical application, injection, or oral administration. Where the lesion is scarred or thickening is observed, topical efficacy is enhanced by perforating the lesion with a needle or scalpel prior to topical application of the ointment, in order to enhance the penetration of the ointment into the lesion. Only one topical application is typically required, and the tissue forming the lesion is expected to turn black and necrotic after about three to four weeks. The dead tissue is peeled away, and the wound site typically heals to completion after another three to four weeks have passed. Even where large lesions have been removed in this manner, there is typically no scarring, and even the hair follicles are restored to full function.

DETAILED DESCRIPTION OF THE PREFERRED EMBODIMENT

Figure 1:
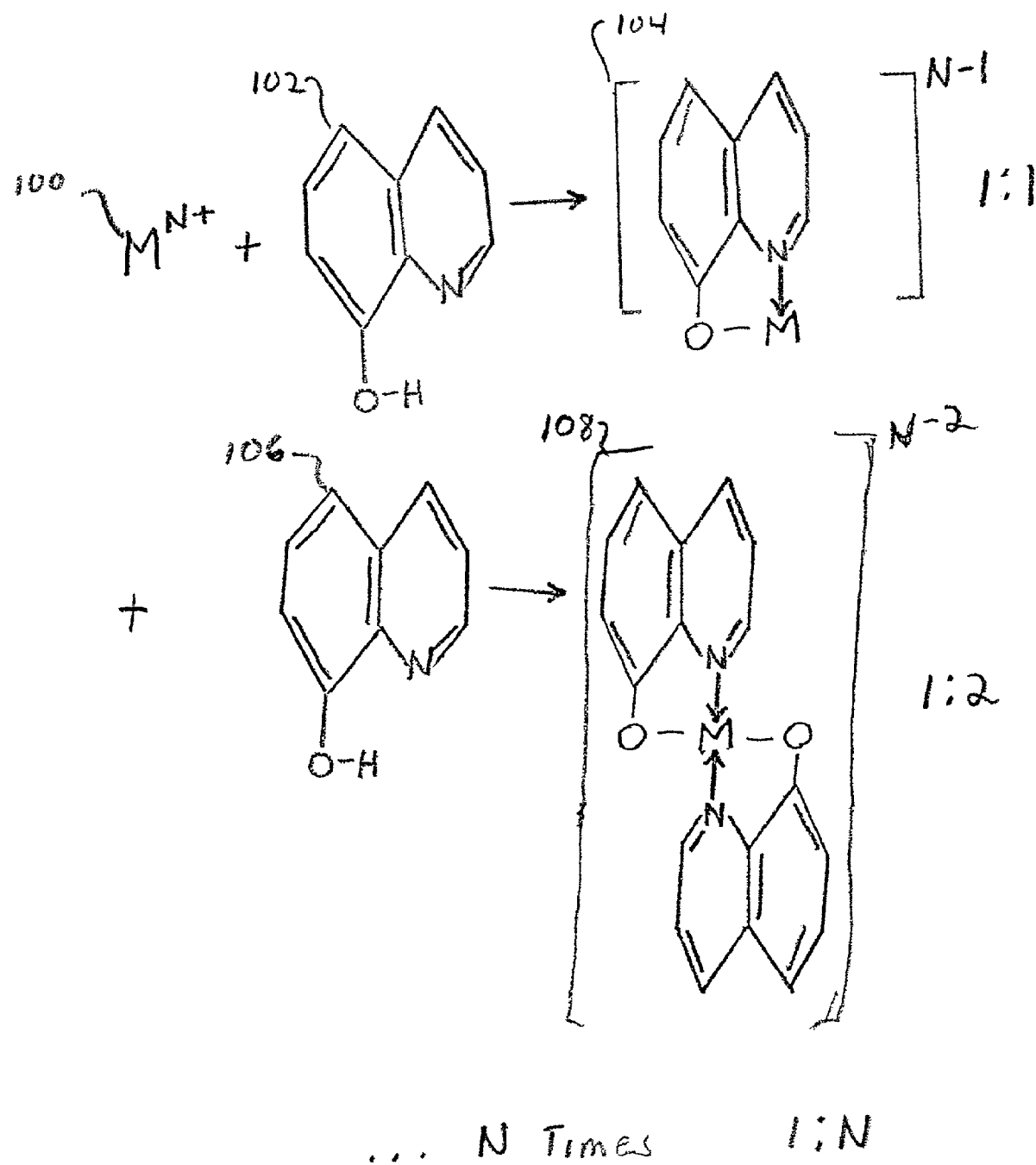
FIG. 1 depicts the celation mechanism between a metal and oxine.

FIG. 1 depicts the chelation mechanism for 8-hydroxyquinoline. A chelatable metal M 100 has an oxidation state of N+. The chelatable metal M 100 reacts with 8-hydroxyquinoline 104 to produce a 1:1 metal oxinate 104 having a valence of N−1. A second 8-hydroxyquinoline molecule 106 reacts with the 1:1 metal oxinate 104 to produce a 1:2 metal oxinate 108. This process is repeated N times until the resultant oxinate has a neutral charge. even then there is coordinate attraction between the metal M 100 and the heterocyclic nitrogen atoms in other oxinates. The lowest ratio oxinates, e.g., the 1:1 oxinate 104, are the most stable products due to the steric hindrance that the large oxinate ligands provide as the reaction proceeds. Thus, if the reaction is limited by the 8-hydroxyquinoline reagent, the lower ratio species will predominate. Oxine has a high avidity for metals, and the reaction goes to substantial completion.

Ionic reaction products, i.e, those having a ratio less than 1:N, are subjected to partition effects where cell membranes regulate the intake of cations. On the other hand, uncharged complexes are liposoluble, and readily penetrate cell membranes in a manner in which the cell cannot regulate. While 8-hydroxyquinoline is normally not toxic, chelated forms of 8-hydroxyquinoline do have cytotoxic effects in mammalian cells. This cytotoxic effect is empirically observed for both the charged and uncharged reaction products.

A general theory of pharmacokinetics in the invention is that abnormal mammalian epithelial cells have membranes which are more permeable to chelated forms of 8-hydroxyquinoline than are normal cell membranes. Thus, the chelated 8-hydroxyquinoline is transported across abnormal cell membranes in a greater concentration than is permitted by normal cell membranes. It follows that topically applied chelated 8-hydroxyquinoline has a greater cytotoxic effect upon the abnormal cells because abnormal cells absorb it in a greater concentration. This theory accounts for the observed selective toxicity to epidermal lesions.

In addition to topical applications of the compositions, nordihydroguiaretic acid is used to stabilize the chelated 8-hydroxyquinoline in solutions that are injected into the patient. Nordihydroguiaretic acid is an antioxidant that protects the chelated oxine compositions against inactivation that, otherwise, might occur due to secretions from the blood that tend to inactivate oxine. Similarly, another antioxidant, sodium ascorbate, is coprecipitated with oxine and zinc chloride from a solution of ethanol and water to form an orally administrable product, which also has in vivo utiility.

Patients sometimes report a burning sensation at the lesion after topical application of the chelated oxinates. Therefore, it is preferred to place an emollient into the composition, in order to sooth the burning sensation. Penetrating agents, such as lecithin or DMSO, are believed to enhance the efficacy of the compositions.

The following working examples set forth preferred methods and materials for use in practicing the invention.

EXAMPLE 1

Preparation of a Zinc-Chelated Liquid Solution of 8-Hydroxyquinoline for Use in Treating Epithelial Lesions Bulk stock solutions were made for later use as intermediates in mixing the final solution. The bulk stock solutions included a gel base solution that was used to stabilize the final product and impart a suitable thickness for the intended environment of use. A lecithin/isopropyl palmitate solution was also prepared.

The gel base solution was prepared by mixing 20 grams (gm) of Pluronic F127™[1] with 0.2 gm potassium sorbate. Purified water was added to bring the total volume to 100 ml. Pluronic F127™[1] is a high molecular weight polyoxyalkylene ether derivative of propylene glycol having water soluble, surface active, and wetting properties. The ingredients were mixed in a Braun mixer, sealed in a bowl, and stored under refrigeration at about 5° C. once all of the granules became wet. The solution was refrigerated to avoid solidification of the gel, which occurs at room temperature.

[1] Pluronic F127 is a trademark of the BASF Corporation located in Parisippany, N.J.

The lecithin/isopropyl palmitate solution was prepared by dispersing 100 gm of granular soya lecithin and 0.66 gm of sorbic acid in isopropyl palmitate (100 gm or 117 ml). The dispersed mixture was allowed to stand overnight at room temperature of about 20° C. A liquid formed having a syrup-like consistency.

A 100 gm aliquot of the gel base solution was mixed with 22 ml of the lecithin/isopropyl palmitate solution and 10 ml of distilled water. The mixture was stirred to visual homogeneity. Ten gm of 8-hydroxyquinoline and 20 gm of $ZnCl_2$ were added to the mixture, which was again stirred to homogeneity.

EXAMPLE 2

Topical Application of a Zinc-Chelated
8-Hydroxyquinoline Solution to Cure Athymic Nude
Mice of Cancerous Lesions Corresponding to
Explanted samples of Human Lung Cancer A live human lung cancer cell line Calu-1 or SW-900, as reported by Fogh, J., et al. 59 J. Natl. Cancer Inst. 221-225 (1977), is an epidural lung cancer having an undifferentiated in vitro cytopathology. Cell lines of this type are known to grow tumors of corresponding cytopathology when explanted into athymic nude mice, as reported by Fogh and Giovanella eds., *The Nude Mouse in Experimental and Clinical Research*, Academic Press, London, pp 235-266 (1978) (see especially p. 239). Athymic nude mice may be purchased from specially maintained breeding colonies throughout the United States, such as the breeding colony at the University of Nevada in Reno, Nev. Athymic nude mice are especially desirable to test the efficacy of anticancer compositions because athymic mice lack immune systems. Thus, the mice do not have immune systems to attack explanted cancers in the mice, and the efficacy of anticancer compositions such cancers is primarily due to the compositions alone.

The test procedures that are outlined below are substantially the same as procedures that have actually been performed on athymic nude mice. The procedures below have been modified slightly to present the most preferred mode of performing the procedures.

One hundred and fifty athymic nude mice are obtained from a reputable supplier, e.g., the breeding colony at the Worchester Institute, in Worchester, Mass. The mice are split into a treatment test population of fifty mice, a no treatment test population of fifty mice, and a control population of fifty mice. The populations are maintained as separate groups using conventional procedures for maintaining breeding colonies of athymic nude mice under sterile conditions.

A human epithelial lung cancer cell line, e.g., the Calu-1, SW-900, or MX-1 lung adenocarcinoma line, is cultured in a suitable growth medium, e.g., 50 ml of Eagle's MEM medium (purchased from Life Technologies, Inc., Gaithersburg, Md.), which is supplemented with 10% fetal calf serum and 50 µg/ml gentamicin from Sigma Chemical Co. of St. Louis, Mo. The cells are maintained in a 5% humidified $CO_2$ atmosphere at 37° C. in 75 $cm^2$ plastic tissue culture flasks, with media passage at 5-7 day intervals.

A sample of approximately five million cancer cells is taken by 20 gauge trocar and extruded into the subcutaneous tissue at the posterior base of the neck on an athymic nude mouse. The procedure is repeated for each member of the treatment and no treatment test populations. Conventional sterile procedures are used while working with the mice to avoid infecting the mice with pathogens other than the cancer cell line. Live tissue from surgical patients having human lung cancer may be substituted for the cultured cell lines.

Approximately one-hundred percent of the mice can be expected to survive the grafting procedure. If proper explantation procedures are used, as will be understood by those who are skilled in those procedures, approximately one-hundred percent of the explanted cancer cells will produce epithelial lesions proximate the site of trocar insertion into the mouse. The explanted cancer is permitted to grow for approximately two to three weeks until a cancerous epithelial lesion of approximately 1.5 to 2 cm in diameter is externally visible.

The untreated test population will typically die within sixty days. Once deaths begin occurring, which is usually within about thirty days, it is preferred to euthanize the entire untreated test population to prevent unnecessary suffering. The deaths typically occur from strangulation due to growth of the cancerous tumor at the base of the neck.

The topical solution that was produced in Example 1 is removed from refrigerated storage and stirred to substantial homogeneity. A cotton swab is dipped into the solution. An athymic nude mouse having a posterior neck lesion approximately 1.5 to 2 cm in diameter is selected from the treatment test population. A needle is used to perforate the epidermal portion of the lesion at locations spaced about one milimeter apart from one another. A swab is used to apply a coating of solution over the entire lesion and extending at least one-half cm beyond the visible margins of the lesion. This procedure is repeated for each member of the treatment test population. A single topical application of the solution is the sole and exclusive time that the solution is applied to the lesions.

The treatment test population is monitored for nine months after topical application of the solution. Notes are taken as to the progress of cancer in the mice. The lesions appear inflamed on the first day after topical application. Three to five days after topical application, the lesions appear black with white streaks on the surface. Eight to ten days after the topical application, the lesions appear black and necrotic. Fourteen to sixteen days after the topical application, the lesions have sloughed off. Pathologic examination of tissue samples taken from ten individual mice at the interior margins of the sloughed lesion confirms that no cancer is visibly apparent at the margins. In thee to four weeks after topical application, the tissue at the former lesion sites has healed to become substantially indistinguishable from normal tissue with no evidence of scarring. The treatment test population exhibits cachexia or a slight emaciation corresponding to an average weight of about 4 to 5 gm less than the control population.

The treatment test population mice and the control population mice are monitored for nine months after topical application of the solution. One-hundred percent of the treatment test population typically survives the procedure with no evidence of cancer after nine months, i.e., the therapeutic index of the solution approximates one hundred percent. This success is contrasted against a one hundred percent mortality in the untreated test population, if the untreated test population has not been euthanized to prevent unwarranted suffering.

EXAMPLE 3

Topical Application of a Zinc -Chelated
8-Hydroxyquinoline Solution to Cure Athymic Nude
Mice of Cancerous Lesions Corresponding to
Explanted Samples of other Human Cancers The procedure of Example 2 is repeated for other cancers including human breast cancer, human colon cancer, and human melanoma. It is noted that lung, breast, and colon cancers are classified as malignant epithelial tumors, while melanoma is a malignant nonepithelial tumor. Thus, the study addresses both epithelial and nonepithelial tumors. Specific cell lines that may be used include SW-613 (breast duct adenoca), SW-620 (colon adenoca), and RPMI-7262 (melanoma). See, for a discussion of these cell lines, Fogh, J., et al. 59 J. Natl. Cancer Inst. 221-225 (1977), and Fogh and Giovanella eds., *The Nude Mouse in Experimental and Clinical Research*, Academic Press, London, pp 235-266 (1978) (see especially pp. 238-239).

The therapeutic index is typically one hundred percent effectiveness against all of these explanted cancers in nude mice, with one hundred percent survivorship through treatment, selectivity for the destruction of diseased tissue alone, and no apparent scarring at the former lesion site. The cancers showed no sign of recurrence in the treated test populations after nine months.

EXAMPLE 4

Prepartion of a Zinc-Chelated 8-Hydroxyquinoline Solution for Injection into Athymic Nude Mice These ingredients are weighed out and combined under sterile conditions: nordihydroguiaretic acid (30 gm), 3% saline in water (30 gm), 8-hydroxyquinoline (10 gm), and $ZnCl_2$ (20 gm). The ingredients are stirred to substantial homogeneity, and stored under refrigeration at about 5 ° C.

EXAMPLE 5

Injection of Zinc-Chelated 8-Hydroxyquinoline Solution to Cure Athymic Nude Mice of Human Cancer Lesions The studies of Examples 2 and 3 are repeated in an identical manner, except the injectable solution of Example 4 is substituted for the topical solution of Example 1. In each case, a one-half ml quantity of the Example 4 solution is injected directly into subcutaneous tissue proximate the lesion.

The therapeutic index of the injected solution is typically one-hundred percent effectiveness against all of the explanted lung, breast, colon, and melanoma cancers in athymic nude mice, with one hundred percent survivorship through treatment, and no apparent scarring at the former lesion site. The cancers showed no sign of recurrence in the treated test populations after nine months. The therapeutic effects are superior with necrotic effects being observed at the lesion site approximately three days sooner than in the case of the topical ointment.

EXAMPLE 6

Various Formulations of Chelated 8-Hydroxyquinoline Solutions for Use in the Treatment of Cancerous and Precancerous Epithelial Lesion Table 1 below shows various topical product formulations that may be used to dispense therapeutically effective amounts of 8-hydroxyquinoline and zinc chloride. In Table 1 below, "NDGA" represents nordihydroguiaretic acid. "P20%" represents a solution that contains 20% Pluronic 127 NF[1] by weight, in addition to 0.2% potassium sorbate, and 79.8% distilled water. "P30%" represents a solution that contains 30% Pluronic 127 NF[1] by weight, in addition to 0.2% potassium sorbate, and 69.8% distilled water. "P40%" represents a solution that contains 40% Pluronic 127 NF[1] by weight, in addition to 0.2% potassium sorbate, and 59.8% distilled water. "Lec/ls" refers to a solution that contains 100 gm granular soya lecithin, 100 gm isopropyl palmitate, and 0.66 gm sorbic acid.

[1] Pluronic F127 is a trademark of the BASF Corporation located in Parisippany, N.J.

The Pluronic 127 NF[1] solutions are preferred due to pharmacoactivity that facilitates the transportation of large molecules through epidermal tissues. In this manner, the gels function as adjuvants to improve the efficacy of chelated 8-hydroxyquinoline compositions. A disadvantage of Pluronic 127 NF[1] gels is that they must be made and stored at temperatures less than 40° F. because the gels solidify at higher temperatures. Other gel bases may be used including Aqua Base or other polymers dispersed in a suitable solvent for 8-hydroxyquinoline. Lecithin and other penetrants including dimethyl sulfoxide may also be used within prescribed limits to enhance the activity of the chelated oxyquinoline compositions. In Table 1, the term "q.s." is used to show that a sufficient quantity of gel was added

[1] Pluronic F127 is a trademark of the BASF Corporation located in Parisippany, N.J. to bring the total weight of the combined ingredients to the weight shown in the column, i.e., 100 gm.

TABLE 1

| | TOPICAL OINTMENT PRODUCT FORMULATIONS | | | | | | | | | |
|---|---|---|---|---|---|---|---|---|---|---|
| Sample | 8-hydroxy-quinoline (gm) | Zinc Chloride (gm) | Distilled Water (ml) | NDGA (gm) | P20% (q.s. gm) | P30% (q.s. gm) | P40% (q.s. gm) | Quercetin (gm) | Lec/ls (ml) | $Sb_2S_3$ (gm) |
| A | — | 60 | 30 | — | — | — | — | — | — | 40 |
| B | 10 | 20 | 10 | — | 100 | — | — | — | 22 | — |
| C | 10 | 20 | 10 | — | — | — | 100 | — | 22 | — |
| D | 10 | 20 | 10 | — | 100 | — | — | — | 20 | — |
| E | 10 | 20 | 10 | 10 | 100 | — | — | — | 18 | — |
| F | — | 10 | 10 | 10 | 100 | — | — | 10 | 18 | — |
| G | 10 | 20 | 10 | — | 100 | — | — | — | 15 | — |
| H | 10 | 20 | 10 | — | 100 | — | — | — | 15 | — |
| I | 10 | 20 | 10 | — | — | 100 | — | — | 18 | — |
| J | — | 67.5 | 35 | 13.75 | — | — | — | 17.5 | — | — |

EXAMPLE 7

Use of Zinc-Chelated 8-Hydroxyquinoline Solutions to Treat Lesions in Humans

A solution corresponding to Sample B from Table 1 in Example 6 was applied topically to treat cancerous lesions, precancerous lesions, and warts on human patients. Treatment included a single topical application of the ointment, and was successful in every case. Table 2 below lists the types of lesions that were successfully treated, as well as the number of lesions that were successfully treated. The total elapsed time from the topical application to sloughing of the diseased tissue was approximately twelve days in each case. The patients who underwent treatment for venereal warts reported much less discomfort than normally exists for chemical removal of venereal warts.

TABLE 2

SUCCESSFUL USE OF CHELATED 8-HYDROXYQUINOLINE IN HUMANS

| Lesion Type | Number of Lesions | Location |
|---|---|---|
| Basal cell | 2 | Left side of nose |
| | 1 | Right ear |
| | 7 | Right forehead |
| | 2 | Forehead |
| | 1 | Left Cheek |
| | 3 | Scalp |
| | 1 | Neck |
| | 3 | Face |
| | 2 | Hands |
| | 1 | Head |
| | 2 | Left mandibular area |
| | 1 | Arm |
| | 2 | Left Temple |
| | 4 | (Unspecified) |
| Solar Keratosis | 2 | Head |
| | 1 | Right forearm |
| Human papilloma virus | 1 | Left chest |
| | 1 | (Unspecified) |
| Venereal warts | 2 | Penis |
| | 1 | (Unspecified) |
| Male veruoca warts | 1 | (Unspecificed) |
| Kaposi's sarcoma | 1 | Arm |
| | 1 | Leg |
| | 1 | Wrist |
| | 1 | Foot |

EXAMPLE 8

Use of Zinc-Chelated 8-Hydroxyquinoline Solutions to Treat Lesions in Animals

A solution corresponding to sample 73 from Table 1 in Example 6 was applied topically to treat cancerous lesions and precancerous lesions on animals. Treatment was successful in every case, with the exception of one cat that died of sarcoma before the treatment was concluded. Table 3 below lists the types of lesions that were successfully treated and the type of animal on which treatment was successful.

TABLE 3

SUCCESSFUL USE OF CHELATED 8-HYDROXYQUINOLINE IN ANIMALS

| Lesion Type | Type of Animal |
|---|---|
| Eye cancer | 3 Cows |
| Sarcoid | 4 Horses |
| Sarcoma | 1 Dog (leg) |
| Malignant melanoma | 2 Horses |
| Rectal adenoma | 1 Dog |
| Sebaceous gland adenoma | 1 Dog |
| Histiocytoma | 1 Dog |
| Sebaceous adenoma (two applications) | 1 Dog |
| Sarcoma | 2 Cats (one died before end of treatment) |

EXAMPLE 9

Titration of Zinc-Chelated 8-Hydroxyquinoline Solution to Reduce Escharotic Effects while Optimizing Therapeutic Effect Three samples of ointment were prepared corresponding to Sample B from Table 1, except the lecithin/palmitate was not added and the weight percentage amount of zinc chloride comprised 20%, 40%, 55% and 75%, respectively, for the samples. The solutions were each applied to a population of twenty five athymic nude mice with explanted lung cancer in the manner of Example 1. The 55% and 75% samples produced substantially immediate chemical escharotic effects. The 40% sample produced heightened redness proximate the lesion site, and was therapeutically effective. At a 40% concentration, the ointment has the effect of selectively eating away the lesion before the underlying tissue has opportunity to regenerate. The 20% sample was therapeutically effective without burning, and the underlying tissue has a chance to regenerate without the formation of an eschar, i.e., the 20% solution does not tend to leave a hole at the lesion site, rather, no eschar is produced because the necrotic lesion tissue remains in place while the underlying tissue at least partially regenerates.

It is preferred not to use the Pluronic gels at high concentrations of $ZnCl_2$ because it has been observed that the gels degrade over time, and it is believed that the gel degradation is due to an altered solution pH.

EXAMPLE 10

Use of Zinc-Chelated 8-Hydroxyquinoline on Human Patients in a Clinical Evaluation Patient 1: A man entered a clinic in Mexico City to request treatment of a large growth on his right wrist. The growth was approximately eleven centimeters in diameter and circumscribed more than fifty percent of the wrist. The size and location of the growth meant that surgery would leave the man with impaired wrist movement. The growth was diagnosed as basal cell carcinoma. A solution corresponding to Sample B of Table 1 was applied to the carcinoma using a cotton swab. The patient was monitored for two months. The patient complained of a burning sensation. The growth appeared red and inflamed at its margins on the first day after treatment. One week later, the growth appeared black and necrotic. Two weeks after treatment, the growth was black and necrotic. The dead growth was peeled away using forceps. pathologic examination of tissue from the wrist confirmed that basal cell carcinoma was absent from healthy tissues at the margin of the wound. Six weeks after treatment, the wound site appeared as healthy tissue with no sign of basal cell carcinoma or scarring. Hair follicles were intact at the site of the former wound and basal cell carcinoma. The man retained full function in the affected wrist.

Patient 2: A woman entered a clinic in Mexico City with a basal cell carcinoma approximately on inch below the corner of her left eye. The growth was approximately one-half inch in diameter. The surgical prognosis was that removal of the growth would leave the woman with partial paralysis of the face and eye muscles. A solution corresponding to solution #73 was applied to the carcinoma using a cotton swab. The patient was monitored for two months. The patient complained of a burning sensation. The growth appeared red and inflamed at its margins on the first day after treatment. One week later, the growth appeared black and necrotic. Two weeks after treatment, the growth was black and necrotic. The dead growth was peeled away using forceps. pathologic examination of tissue from the wrist confirmed that basal cell carcinoma was absent from healthy tissues at the margin of the wound. Six weeks after treatment, the wound site appeared as healthy tissue with no sign of basal cell carcinoma or scarring. Hair follicles were intact at the site of the former wound and basal cell carcinoma. The woman retained full function in muscles of the face and eye.

EXAMPLE 11

Preparation of an Orally Administrable Composition

A solution was mixed to include equal 33 gram weights of 8-hydroxyquinoline, sodium ascorbate, and zinc chloride in 90% ethanol with sufficient water added to just dissolve the ingredients at 110° F. The mixture stood to ambient room temperature under a ventilation hood for twenty four hours. A vacuum aspirator was used to remove remaining liquid while coprecipitating the remaining moieties from solution. The precipitate was scraped from the beaker, supplemented with 5 grams of ascorbic acid, and ground to homogeneity with mortar and pestle.

Those skilled in the art will understand that the preferred embodiments described above may be subjected to apparent modifications without departing from the true scope and spirit of the invention. The inventors, accordingly, hereby state their intention to rely upon the Doctrine of Equivalents, in order to protect their full rights in the invention.

The invention claimed is:

1. A composition for use in treating epithelial lesions formed of a combination of ingredients comprising:

8-hydroxyquinoline in an amount of at least five percent of the composition by weight;

zinc bonded to said 8-hydroxyquinoline, the zinc being present in a concentration of at least five percent by weight of the composition and less than an amount that produces an eschar in healthy mammalian tissues; and a carrier, the composition being a pharmaceutical grade material.

2. The composition as set forth in claim 1, wherein zinc is present in a molar ratio (8-hydroxyquinoline:zinc) ranging from 1:1 to 1:3.

3. The composition as set forth in claim 2 wherein said molar ratio is about 1:2.

4. The composition as set forth in claim 1 wherein the zinc is provided in the composition as zinc chloride in an amount ranging up to forty percent by weight of said composition by weight.

5. The composition as set forth in claim 1 wherein the zinc is provided in the composition as zinc chloride in an amount ranging up to twenty percent of said composition by weight.

6. The composition as set forth in claim 1, wherein said carrier comprises a gel.

7. The composition as set forth in claim 6 wherein said gel comprises a polyoxyalkylene ether derivative of propylene glycol.

8. The composition as set forth in claim 1 wherein said carrier contains a penetrant selected from the group consisting of lecithin and dimethyl sulfoxide.

9. The composition as set forth in claim 8 wherein said penetrant is lecithin.

10. The composition as set forth in claim 8 wherein said penetrant is dimethyl sulfoxide.

11. The composition as set forth in claim 1 wherein said carrier contains an antioxidant selected from the group consisting of nordihydroguiaretic acid and ascorbic acid.

12. The composition as set forth in claim 11 wherein said antioxidant includes at least nordihydroguiaretic acid.

13. The composition as set forth in claim 11 wherein said antioxidant includes at least ascorbic acid.

14. The composition as set forth in claim 1 wherein said carrier consists essentially of an antioxidant selected from the group consisting of nordihydroguiaretic acid and ascorbic acid.

15. The composition as set forth in claim 14 wherein said antioxidant consists essentially of ascorbic acid.

16. The composition as set forth in claim 14 wherein the antioxidant consists essentially of nordihydroguiaretic acid.

* * * * *